(12) United States Patent
Goetchius

(10) Patent No.: US 7,444,874 B2
(45) Date of Patent: Nov. 4, 2008

(54) METHOD OF DETERMINING DAMPING OF AN ARTICLE OF MANUFACTURE AND SYSTEM FOR DETERMINING DAMPING PERFORMANCE

(75) Inventor: Gregory M Goetchius, Oakland, MI (US)

(73) Assignee: Material Sciences Corporation, Elk Grove Village, IL (US)

( * ) Notice: Subject to any disclaimer, the term of this patent is extended or adjusted under 35 U.S.C. 154(b) by 302 days.

(21) Appl. No.: 11/428,451

(22) Filed: Jul. 3, 2006

(65) Prior Publication Data

US 2008/0000300 A1 Jan. 3, 2008

(51) Int. Cl.
*G01N 29/12* (2006.01)
*G01H 9/00* (2006.01)
*G01H 13/00* (2006.01)

(52) U.S. Cl. .......................................... 73/579; 73/657
(58) Field of Classification Search .................. 73/579, 73/655, 657
See application file for complete search history.

(56) References Cited

U.S. PATENT DOCUMENTS

| | | | | |
|---|---|---|---|---|
| 5,144,838 A | * | 9/1992 | Tsuboi | 73/579 |
| 5,520,052 A | * | 5/1996 | Pechersky | 73/579 |
| 5,533,399 A | * | 7/1996 | Gibson et al. | 73/579 |
| 5,821,424 A | * | 10/1998 | Rodriguez | 73/657 |
| 6,085,593 A | * | 7/2000 | Pileri et al. | 73/663 |
| 6,532,818 B2 | | 3/2003 | Blankenship | |
| 6,843,128 B2 | * | 1/2005 | Chen et al. | 73/574 |

OTHER PUBLICATIONS

Standard Test Method for Measuring Vibration-Damping Properties of Materials E 756-98, Annual Book of ASTM Standards, Nov. 1998, American Society for Testing and Materials, West Conshohoken, PA.

* cited by examiner

*Primary Examiner*—Hezron E. Williams
*Assistant Examiner*—Rose M Miller
(74) *Attorney, Agent, or Firm*—Quinn Law Group, PLLC; Christopher W. Quinn

(57) ABSTRACT

A method of determining damping performance of an article of manufacture includes moving an article of manufacture along a production line, directing a laser beam at a surface of the moving article and then measuring the velocity of a reflection of the beam simultaneously with measuring vibrational excitation in an environment of the production line. The method then includes calculating the damping performance of the moving article of manufacture based on the velocity and vibrational excitation measurements. The calculated damping performance may also be based on a predetermined correlation factor of damping performance of a reference article calculated based on the online system compared with damping performance of the reference article calculated in a controlled offline environment. A system for determining damping performance online is also provided.

11 Claims, 2 Drawing Sheets

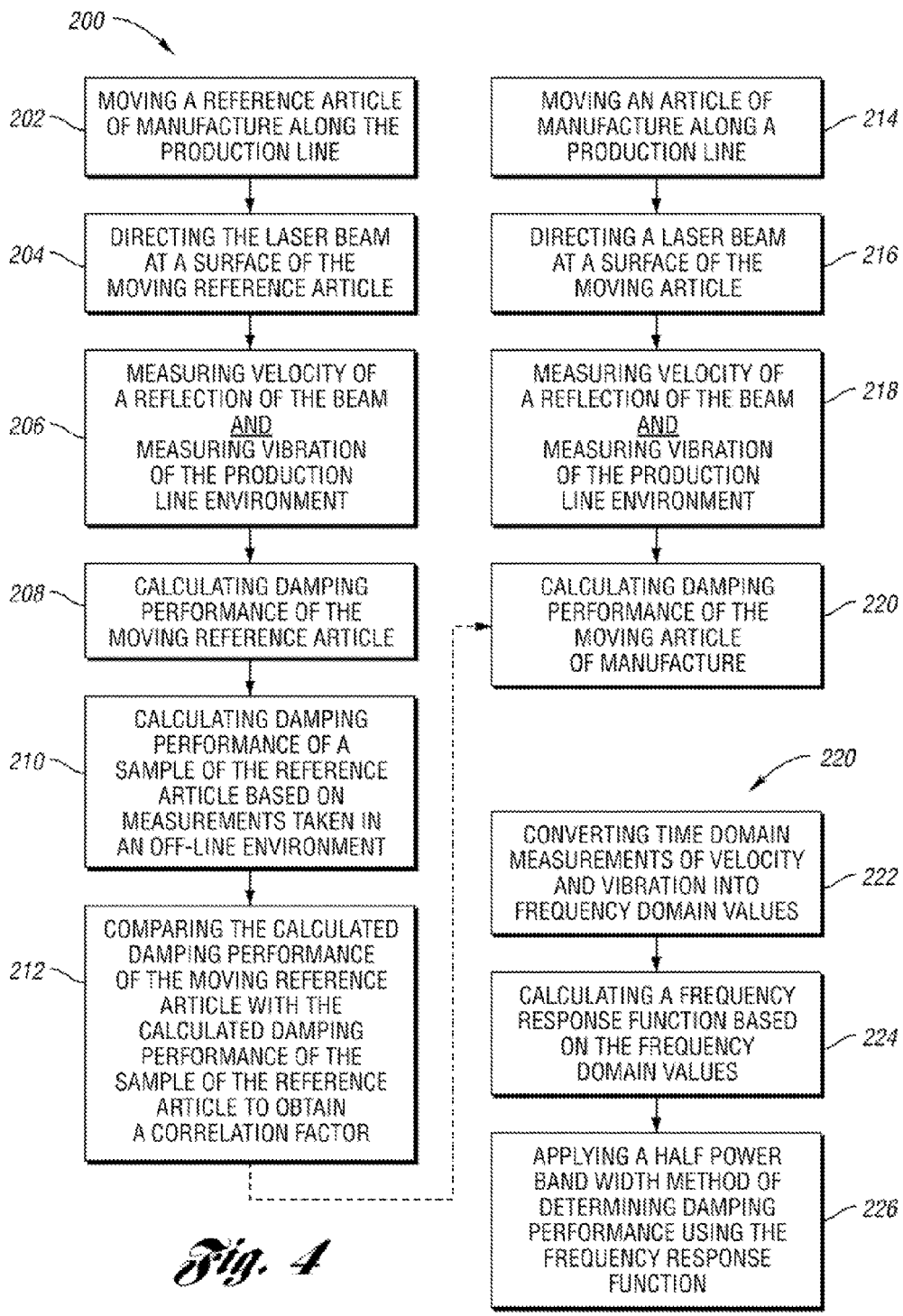

METHOD OF DETERMINING DAMPING OF AN ARTICLE OF MANUFACTURE AND SYSTEM FOR DETERMINING DAMPING PERFORMANCE

TECHNICAL FIELD

The invention relates to determining the damping performance of an article of manufacture; specifically, a method and a system for determining damping while the article is moving along a production line.

BACKGROUND OF THE INVENTION

Many articles of manufacture are specifically designed to meet required damping levels in order to deaden structural or acoustical vibration. For example, laminated sheet metal is utilized to deaden noise in various applications, such as in automotive panels and consumer appliances. Damping of such articles has heretofore typically been determined according to a strictly controlled procedure carried out offline (i.e., not on the production line) utilizing carefully prepared test samples. Often, the test samples are made by hand in a laboratory and may not accurately reflect the damping capability of the actual article of manufacture formed by manufacturing processes on the production line. Standard procedures for determining damping utilize a transfer function, plotted as a response curve, which represents the output or response of the test sample to a known, controlled excitation or input. A determination of damping capability is derived from the transfer function by measuring the amplitude of the peaks in the response curve.

SUMMARY OF THE INVENTION

A method is provided for determining damping of an article of manufacture based on measurements taken as the article moves along a production line, i.e., an "online" damping determination. A damping determination system is also provided. Because the article is moving along the production line, fixed vibration transducers cannot be attached to the article; thus, it is not possible to induce a known excitation in the article on which to base a damping determination. Under the method, an excitation in the surrounding environment of the production line is measured and used as an assumed input excitation for determining damping. The method provides a way to rectify any systemic difference in damping determination made online versus that made offline due to the reliance on assumed (rather than known) vibrational excitation in the online determination. Specifically, a reference article is subjected to the online method to establish an online damping determination for the reference article. A sample of the reference article is then subjected to a controlled, offline method of determining damping and the online damping determination is then compared with the online determination to establish a correlation factor. The correlation factor is predetermined, so that it may be applied to the online damping determination of the production article in real time (i.e., as the article is being manufactured). The correlation factor allows approximation of an equivalent offline damping determination based on the online determination, although the production article need never be subjected to the offline determination. The damping determination is provided by a controller in real time, i.e., as the article is being processed along the production line. Thus, any nonconformance with desired damping performance is immediately known, allowing for earlier correction of any processing inaccuracies affecting the damping performance and thus potentially reducing manufacturing costs. Additionally, the online testing method and system allow for continuous testing of the entire length of the article of manufacture, and thus may be more reliable than offline determinations based only on a small sample of an article that may not be representative of the remainder of the article.

The method of determining damping performance of an article of manufacture includes moving an article of manufacture along a production line, directing a laser beam at a surface of the moving article and then measuring the velocity of a reflection of the beam simultaneously with measuring vibrational excitation in an environment of the production line. The method then includes calculating the damping performance of the moving article of manufacture based on the velocity and vibrational excitation measurements. Finally, the calculated damping performance may also be based on a predetermined correlation factor of damping performance of a reference article calculated based on the online system compared with damping performance of the reference article calculated in an offline environment.

A system of determining damping performance includes a vibrational transducer configured to direct the laser beam at the surface of the moving article of manufacture and to measure the velocity of the reflected beam. The system also includes either or both of an accelerometer and a microphone positioned to measure vibrational excitation in an environment surrounding the article of manufacture. Finally, the system includes a controller operatively connected to the vibrational transducer and with the accelerometer and/or microphone that is configured to calculate damping performance of the moving article based on the measured velocity and vibrational excitation.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 4 is a flow chart illustrating a method of determining damping performance of a moving article of manufacture according to the invention; and FIG. 5 is a flow chart illustrating substeps carried out within the step of calculating damping performance of the moving article of manufacture illustrated in FIG. 4.

DESCRIPTION OF THE PREFERRED EMBODIMENTS

Figure 1:
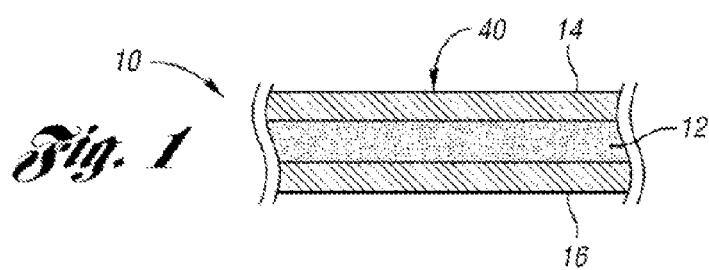
FIG. 1 is a schematic cross-sectional illustration in fragmentary view of laminated steel with damping capability.

Referring to the drawings, wherein like reference numbers represent like components, FIG. 1 illustrates an article of manufacture 10 that is laminated steel. The laminated steel has a viscoelastic layer 12 sandwiched between first and second steel layers 14, 16. The viscoelastic layer 12 preferably spans the entirety of both steel layers 14, 16. An example of commercially available laminated steel is the product Quiet Steel® from Material Sciences Corporation of Elk Grove Village, Ill., although other laminated steel may be utilized within the scope of the invention. Laminated steel such as Quiet Steel® is useful in automotive applications to dampen noise and structural vibrations. It should be appreciated that the invention is not limited to determining the damping performance of laminated steel, and that the damping performance of other articles of manufacture may be determined under the method and using the system described herein. It is important to be able to determine damping performance in an accurate and efficient manner. Utilizing the system 18 depicted in FIG. 2 and the method illustrated in FIGS. 4 and 5 allows for a continuous damping performance assessment of articles of manufacture on the factory production line, as they are being produced. Online damping determination provides a quicker determination of noncompliance with desired damping performance and thus allows a quicker correction of factors contributing to noncompliance.

Figure 2:
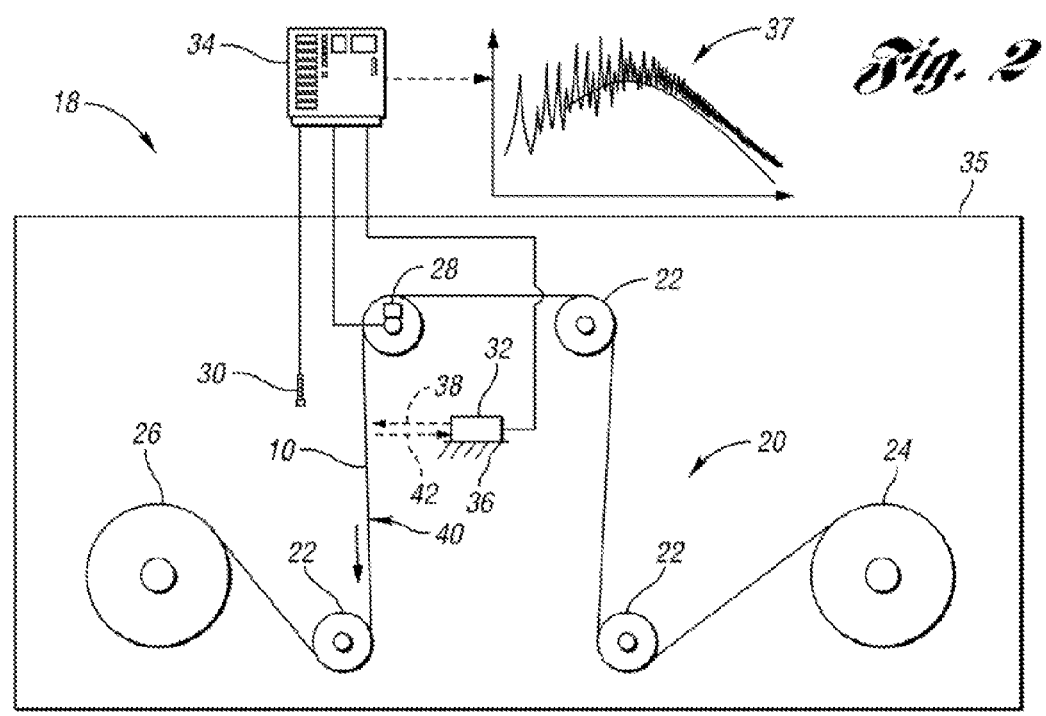
FIG. 2 is a schematic representation of a system for determining damping performance of a moving article of manufacture, which in this embodiment is the laminated steel of FIG. 1 during production (i.e., online)

In FIG. 2, the article of manufacture 10 is shown as it is being produced, moving along a production line 20. The production line 20 includes various machinery that supports, forms and processes the article of manufacture 10 such as rollers 22, which move the article of manufacture 10 from a pre-production state 24 (illustrated at the right as a coiled state), representing the steel layers 14, 16, to a completed state 26 in which the viscoelastic layer 12 has been applied to complete the laminated steel 10, which is then recoiled in preparation for shipping. Other machinery is also utilized along the production line to manufacture the article of manufacture 10, but is not shown for purposes of clarity.

During the production of the article of manufacture 10, as it is moving along the production line 20, the article of manufacture is subjected to varying levels of vibrational excitation due to noise and structural vibration in the production line environment 35. It is not practical to stop the line in order to measure and apply a controlled vibrational input to the article of manufacture to determine damping performance. Accordingly, the system 18 measures the vibrational excitation in the environment (i.e., the vicinity) of the production line 35 and utilizes this measured excitation as the vibrational input in calculating the damping performance of the article of manufacture 10. More specifically, the system 18 includes an accelerometer 28, a microphone 30, a vibration transducer 32 and a controller 34. The accelerometer 28 and the microphone 30 are positioned in the vicinity of the production line 20 such that they can measure vibrational excitation in the environment 35 of the production line. (In FIG. 2, the controller 34 appears outside of the environment 35, but it could alternatively be within the environment 35. That is, the controller 34 could be remotely placed in a separate room away from the production line 20 as long as it is operatively connected to the accelerometer 28, the microphone 30 and the vibrational transducer 32.)

The accelerometer 28 is shown mounted to a roller 22, but may be placed in other alternative locations within the scope of the invention. The microphone 30 measures acoustical vibration in the air surrounding the article of manufacture 10. The accelerometer 28 measures structural vibration in the environment 35. The accelerometer 28 and the microphone 30 are in signal communication with the controller 34.

The vibration transducer 32 is preferably a non-contact, single point laser vibrometer mounted on supporting structure 36 such that it directs a laser beam 38 substantially normal to a surface 40 of the moving article of manufacture 10. The surface 40 is also indicated in FIG. 1. The surface 40 is a reflecting surface, and causes a reflection 42 of the laser beam 38. The reflection 42 is directed back at the vibration transducer 32 which measures the velocity of the reflection 42. The velocity measurement, which is taken continuously as the article of manufacture 10 passes along the production line 20, is then sent to the controller 34, which is in signal communication with the vibration transducer 36. The vibration of the article of manufacture 10 is related to the velocity of the reflection of the beam, as is understood by those skilled in the art.

Assuming that the vibrational excitation in the vicinity of the production line 20, as monitored by the accelerometer 28 and the microphone 30, is applied to the article of manufacturer 10, the ability of the article of manufacture 10 to dampen some of the excitation can be monitored by the vibrational transducer 32. The controller 34 is configured with algorithms which calculate the damping performance of the article of manufacture 10 based on the measured velocity and the measured vibrational excitation.

The method of calculating the damping performance based on these measurements will now be described. The output signal of the vibration transducer 32 is a time domain signal, as are the output signals of the accelerometer 28 and the microphone 30. Each of these output signals are received as inputs by the controller 34. In order to estimate damping performance, known methods of calculation, such as the "Half Band-Width Method" described in ASTM Standard E756, require a Frequency Response Function (FRF) 37 (i.e., the response of the article of manufacture 10 to a known input, wherein the response of the article of manufacture (i.e., the output) and the vibrational excitation (i.e., the input or inputs) are both in the frequency domain. Accordingly, the time domain signals from the vibration transducer 32, the accelerometer 28 and the microphone 30 are first converted to digital signals using standard digital signal processing (DSP) hardware included within the controller 34. The digital signals are then converted to the frequency domain using standard Fast Fourier Transform (FFT) algorithms included in the controller 34. A FRF 37 then can be calculated and analyzed according to the chosen method of damping calculation, such as the Half Band-Width method.

As stated above, the measured vibrational inputs in the system 18 are obtained from the microphone 30 and the accelerometer 28, both of which are somewhat spaced from the article of manufacture 10. These inputs are thus only approximations of the level of vibrational excitation actually experienced by the article of manufacture 10. In order to correct for the potential inaccuracy of a damping determination made in reliance on these online, environmental inputs, a correlation factor is determined by comparing the damping determination for an article based on the online measurement system 18 and a damping determination made in a controlled, offline environment based on a known input applied to the same article. The correlation factor can then be applied in calculating the damping determination of another article based on the online system 18. The correlation factor is predetermined based on damping calculations performed on a reference article of manufacture processed along the production line 20 and tested in the offline measurement system of FIG. 3. In this way, the correlation factor may be programmed into the controller 34 and automatically applied in real time when determining the damping performance of the article of manufacture 10 as it is processed.

Figure 3:
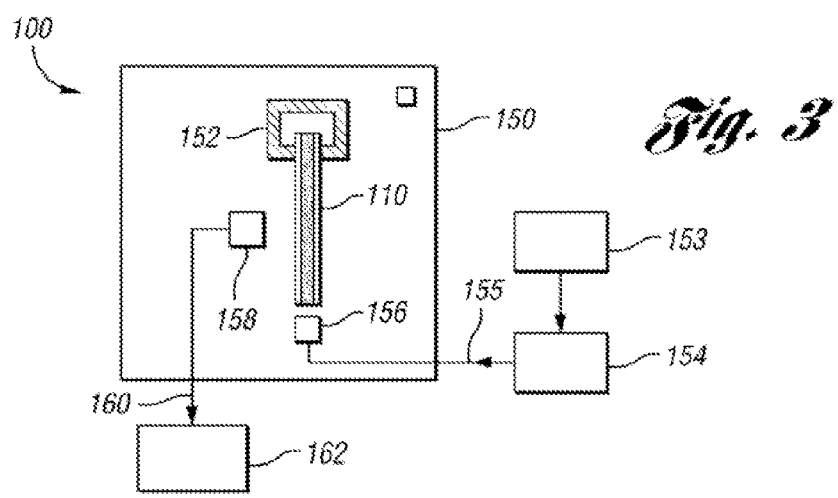
FIG. 3 is a schematic representation of a controlled, offline system for determining damping performance of a test sample of a reference article of manufacture.

Referring to FIG. 3, an offline damping measurement system 100 is illustrated. This type of system is well known in the art and is described in American Society for Testing and Materials (ASTM) Standard E756. The system 100 provides a controlled, offline environment 150 in which a sample of a reference article of manufacture 110 is placed. The environment 150 is controlled such that unwanted vibrational excitation is excluded. The reference article of manufacture 110 may be a sample from another laminated steel roll produced along the production line 20 and on which an online damping determination has already been made according to the vibrational transducer 32, the accelerometer 28 and the microphone 30 of the system 18 of FIG. 2. The sample 110 is held in a rigid test fixture such as a clamp 152. A signal generator 153 and an amplifier 154 provide a known input signal 155 which is applied to the sample 110 as vibrational excitation via an excitation transducer 156 such that the sample 110 is subjected to a known level of excitation in the controlled environment 150. The vibration response of the sample 110 is measured via a response transducer 158 which sends an output signal 160 proportional to the response to a spectrum analyzer 162. Those skilled in the art understand how to determine damping performance under a variety of methods such as the Half-Width Band Method using the input signal 155 and the output signal 160. The measurement obtained from system 18 may be compared to that obtained from system 100 to establish a correlation factor of online system based damping determination to offline system based damping determination. This correlation factor is then included in the algorithm stored in the controller 34 to be applied when determining the damping performance using the online system 18, such as in determining the damping performance of the article of manufacture 10 in FIG. 2.

Referring now to FIG. 4, a method of determining damping performance 200 is illustrated and will be described with respect to the online system 18 and the offline system 200 described above with respect to FIGS. 2 and 3. The method 200 includes step 214, moving an article of manufacture, such as sheet laminate 10 along a production line 20. As the article of manufacture moves past, a laser beam is directed at a surface of the moving article under step 216. Step 218 is then performed, which involves two simultaneous sub steps: measuring velocity of a reflection of the beam and measuring vibrational excitation in the production line environment. The velocity is measured via the vibrational transducer 32 of FIG. 2 which emitted the laser beam. The vibrational excitation in the production line environment is measured by one or more means, which in FIG. 2 include an accelerometer 28 and a microphone 30. Finally, the damping performance of the moving article of manufacture is calculated under step 220, by the controller 34 based on signals received from the vibrational transducer 32 indicative of the measured velocity and signals received from the accelerometer 28 and the microphone 30 indicative of the measured vibrational excitation.

Preferably, the damping performance calculated in step 220 also applies the correlation factor between damping performance calculated in the online environment and damping performance calculated in the offline environment 150 of FIG. 3. If so, steps 202 to 212 must be performed prior to steps 214, such that the correlation factor can be included in the continuous calculations of online damping performance. Accordingly, the method 200 also includes moving a reference article of manufacture along the production line, step 202, and directing a laser beam at a surface of the moving reference article, step 204. Next, under step 206, velocity of a reflection of the laser beam and vibrational excitation in the production line environment are simultaneously measured. The damping performance of the moving reference article is then calculated under step 208 based on the measurements of step 206. A sample of the reference article of manufacture is then taken to a controlled, offline environment 150 (see FIG. 3) and damping is calculated under step 210 based on measurements taken in this offline environment. Under step 212, the damping determination of the moving article of manufacture calculated in the online environment under steps 202 to 208 is compared with the damping determination of the sample of the reference article as determined in the offline environment 150 in FIG. 3 under the system 100 of FIG. 3 to determine a correlation factor. The correlation factor determined under step 212 is sent to the controller 34 of FIG. 1 and is incorporated into step 220, when calculating damping determination of the moving article of manufacture, so that the calculated determination is a more accurate representation of the actual damping properties of the article of manufacture.

Referring to FIG. 5, step 220, calculating damping performance is illustrated in greater detail. Step 220 includes step 222, converting time domain measurements of velocity and vibrational excitation into frequency domain values. In step 224, a FRF is then calculated based on the frequency domain values determined in step 222. Finally, under step 226, a half power band width method of determining damping performance is applied to the FRF.

The system 18 and the method 220 discussed herein allow continuous monitoring of damping performance during online production of an article of manufacture. This promotes efficiency and better compliance with target damping performance.

While the best modes for carrying out the invention have been described in detail, those familiar with the art to which this invention relates will recognize various alternative designs and embodiments for practicing the invention within the scope of the appended claims.

The invention claimed is:

1. A method of determining damping performance comprising:
    moving an article of manufacture along a production line;
    directing a laser beam at a surface of said moving article;
    measuring velocity of a reflection of said beam reflected off of said surface;
    simultaneously with said measuring velocity, measuring vibrational excitation in an environment of said production line; and
    calculating damping performance of said moving article of manufacture based on said measured velocity and said measured vibrational excitation.

2. The method of claim 1, wherein said measured velocity and said measured vibrational excitation are time domain measurements; and wherein said calculating said damping performance includes converting said time domain measurements into frequency domain values.

3. The method of claim 2, wherein said calculating damping performance includes calculating a frequency response function based on said frequency domain values.

4. The method of claim 3, wherein said calculating damping performance is according to a half power band width method using said frequency response function values.

5. The method of claim 1, further comprising:
    prior to said moving an article of manufacture, moving a reference article of manufacture along said production line;
    directing said laser beam at a surface of said moving reference article of manufacture;
    measuring velocity of a reflection of said beam reflected off of said surface of said moving reference article of manufacture;
    simultaneously with said measuring velocity of said reflection of said beam reflected off of said surface of said moving reference article of manufacture, measuring vibrational excitation in said environment of said production line;

calculating damping performance of said moving reference article of manufacture based on said measured velocity and said measured vibrational excitation of said reference article of manufacture;

calculating damping performance of a sample of said reference article of manufacture based on measurements taken in an offline environment;

comparing said calculated damping performance of said moving reference article of manufacture with said calculated damping performance of said reference article of manufacture in said offline environment to obtain a correlation factor; and wherein said calculated damping performance of said moving article of manufacture is further based on said correlation factor.

6. The method of claim 1, wherein said article of manufacture is laminated sheet metal.

7. A system for determining damping performance of a moving article of manufacture comprising:

a vibrational transducer configured to direct a laser beam at a surface of said moving article of manufacture and to measure velocity of a reflection of said laser beam;

at least one of an accelerometer and a microphone positioned to measure vibrational excitation in an environment surrounding said moving article of manufacture; and a controller operatively connected with said vibrational transducer and with said at least one of an accelerometer and a microphone and configured to calculate a damping performance of said moving article of manufacture based on said measured velocity and said measured vibrational excitation.

8. The system of claim 7, wherein said moving article of manufacture is laminated metal.

9. The system of claim 7, wherein said moving article of manufacture moves along a production line; wherein said production line includes machinery acting on said article of manufacture; wherein said at least one of an accelerometer and a microphone includes an accelerometer operatively connected with said production line to measure vibrational excitation of said machinery.

10. The system of claim 7, wherein said controller is configured with digital signal processing hardware and a Fast Fourier Transform algorithm for calculating said damping performance.

11. A method of determining damping performance comprising:

moving laminated metal along a production line;

directing a laser beam at a surface of said moving laminated metal;

measuring velocity of a reflection of said beam reflected off of said surface;

simultaneously with said measuring velocity step, measuring vibrational excitation in an environment of said production line; and calculating damping performance of said moving laminated metal based on said measured velocity, said measured vibrational excitation, and a predetermined correlation factor of calculated damping performance of a reference article of manufacture moving along said production line to calculated damping performance of said reference article of manufacture calculated in an offline environment.

* * * * *